US006307627B1

United States Patent
Vurens

(10) Patent No.: US 6,307,627 B1
(45) Date of Patent: *Oct. 23, 2001

(54) OPTICAL MEASUREMENT SYSTEM USING POLARIZED LIGHT

(75) Inventor: Gerard H. Vurens, Palo Alto, CA (US)

(73) Assignee: HDI Instrumentation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/441,253

(22) Filed: Nov. 16, 1999

Related U.S. Application Data

(63) Continuation of application No. 09/153,646, filed on Sep. 15, 1998, now Pat. No. 6,134,011, which is a continuation-in-part of application No. 09/090,434, filed on Jun. 4, 1998, now abandoned.
(60) Provisional application No. 60/059,498, filed on Sep. 22, 1997.

(51) Int. Cl.⁷ ............................................. G01J 4/04
(52) U.S. Cl. .................. 356/369; 356/237.2; 356/630; 250/225
(58) Field of Search .................. 356/369, 367, 356/364, 365, 360, 368, 237.1, 237.2–237.16, 630, 631; 250/225

(56) References Cited

U.S. PATENT DOCUMENTS

| | | | |
|---|---|---|---|
| 3,904,293 | 9/1975 | Gee | 356/118 |
| 4,585,348 | 4/1986 | Chastang et al. | 356/369 |
| 4,681,450 | 7/1987 | Azzam | 356/367 |
| 4,872,758 | 10/1989 | Miyazaki et al. | 356/381 |
| 4,893,932 | 1/1990 | Knollenberg | 356/369 |
| 4,908,508 | 3/1990 | Dubbeldam | 250/225 |
| 5,102,222 | 4/1992 | Berger et al. | 356/367 |
| 5,282,217 * | 1/1994 | Yamazaki | 372/31 |
| 5,311,285 | 5/1994 | Oshige et al. | 356/369 |
| 5,335,066 | 8/1994 | Yamada et al. | 356/364 |
| 5,438,415 | 8/1995 | Kazama et al. | 356/369 |
| 5,644,562 | 7/1997 | De Groot | 369/110 |
| 5,726,455 | 3/1998 | Vurens | 250/559.28 |
| 5,790,259 | 8/1998 | Mizuhata et al. | 356/445 |
| 5,835,220 | 11/1998 | Kazama et al. | 356/369 |

OTHER PUBLICATIONS

Azzam, R.M.A. "Ellipsometry" *Handbook of Optics: Devices, Measurements & Properties* vol. II, 2nd edition, Bass, M. et al. (eds.), McGraw–Hill, Inc.: chapter 27, pp. 27.1–27.26 (1995).

Herman, I.P. *Optical Diagnostics for Thin Film Processing*, Academic Press, Inc., San Diego, California: chapter 9.11.2, pp. 435–442 (1996).

Jellison, Gerald E. et al. "Two–channel Polarization Modulation Ellipsometer" *Applied Optics* 29(7):959–974 (1990).

* cited by examiner

Primary Examiner—Hoa Q. Pham

(57) ABSTRACT

An optical measurement system for evaluating the surface of a substrate or the thickness and optical characteristics of a thin film layer overlying the substrate includes a light source for generating a light beam, a static polarizing element for polarizing the light beam emanating from the light source, and a measurement system for measuring the light reflected from the substrate location. The measurement system includes a static beam splitting element for splitting the light reflected from the substrate into s-polarized light and p-polarized light. The measurement system further includes two optical sensors for separately measuring the amplitude of the s-polarized light and the intensity of the p-polarized light. A control system analyzes the measured amplitude of the s-polarized light and the p-polarized to determine changes in the topography of substrate or changes in the thickness or optical characteristics of the thin film layer.

41 Claims, 7 Drawing Sheets

OPTICAL MEASUREMENT SYSTEM USING POLARIZED LIGHT

REFERENCE TO RELATED APPLICATION

This application is a continuation of U.S. patent application Ser. No. 09/153,646, filed Sep. 15, 1998 now U.S. Pat No. 6,134,011, which is a continuation-in-part of U.S. patent application Ser. No. 09/090,434 filed Jun. 4, 1998 now abandoned, which claims the benefit of U.S. Provisional Application No. 60/059,498, filed on Sep. 22, 1997. Each of the above-referenced patent applications is incorporated herein by reference.

BACKGROUND OF THE INVENTION

The present invention relates to measurements of partially light-transmissive thin films or layers of such films, and to measurements of surface topography or detection of surface defects. It specifically relates to optical measurement or detection, and to apparatuses for performing such optical measurement or detection of a thin film or a substrate surface.

A number of common articles of manufacture now have constructions involving thin films formed on relatively large area smooth substrates, and substrates wherein the underlying surface is reflective, possibly conductive, and at least visually smooth if not optically flat. To develop manufacturing processes for reliably fabricating these articles and to inspect them or understand the defects which arise in these articles, it is necessary to observe the thin films and the underlying substrate. These films may be liquid or solid, have a thickness substantially under one wavelength of the observation illumination, and may possess features or defects which are observable only with meticulous methodology against the highly reflective substrate, requiring a special instrument. To detect changes occurring on such a thin surface coating is an even more challenging task.

Various optical diagnostic methods, such as reflection ellipsometry, have been proposed to study thin film layers and surfaces. Reflection ellipsometry is the measurement of the change in polarization of light upon reflection from a specular surface to obtain information about the surface. Conventional automatic ellipsometers employ a rotating optical element, usually a rotating analyzer, to measure the polarization of the specularly reflected light beam. A significant drawback of these ellipsometers is that the instruments are relatively slow and thus are not suitable for real-time analysis.

A somewhat faster ellipsometer, a polarization-modulated ellipsometer (PME), is described in a paper of Jellison and Modine (*Applied Optics,* Vol. 29, No. 7, pg. 959 (March 1990)). This ellipsometer employs a photo-elastic modulator that dynamically elliptically polarizes the light incident on the sample surface and separates the analyzed light into orthogonally polarized beams using a Wollaston prism. The time resolution of this system is limited by the modulation frequency of the phase modulator which is approximately 50 kHz. The optimal time resolution of this type of ellipsometer is described as 10-ms, which remains impractical for real-time or in-situ analysis during processing or, in the case of magnetic storage disks, during use.

As the above described and other prior art devices and methods for performing optical measurement or detection of a thin film or a substrate surface have proven less than optimal, it is an object of the present invention to provide nondestructive diagnostic systems and methods having improved sensitivity, speed, and time resolution.

Another object of the present invention is to provide optical measurement systems and methods in which the surface of a substrate can be analyzed by a single optical scan of the substrate surface.

A further object of the present invention is to provide optical measurement systems and methods for real-time and in situ measurement and detection of changes or defects in a thin film layer and the underlying substrate surface.

Other general and more specific objects of this invention will in part be obvious and will in part be evident from the drawings and the description which follow.

SUMMARY OF THE INVENTION

The present invention is directed to an optical measurement system for evaluating the surface of a substrate or the thickness and optical characteristics of a thin film layer overlying the substrate. The optical measurement system includes a light source for generating a light beam, a static polarizing element for polarizing the light beam emanating from the light source, and a measurement system for measuring the light after interaction with the substrate. The measurement system includes a static beam splitting element for splitting the light after interaction with the substrate into s-polarized light and polarized light. The measurement system further includes two optical sensors for separately measuring the amplitude of the s-polarized light and the intensity of the p-polaxized light. A control system analyzes the measured amplitude of the s-polarized light and the p-polarized to determine changes in the topography of substrate or changes in the thickness or optical characteristics of the thin film layer.

A significant advantage of the optical measurement systems of the present invention is that the amplitude of s-polar and p-polar light components can be measured simultaneously, thereby increasing the speed and time resolution of the system by requiring only a single scan of the substrate to analyze the substrate. In one embodiment, the measurement system is configured to measure the light from the substrate at frequencies greater than 1 kHz. In preferred embodiments of the inventions the speed of the system can be improved to 10 MHz.

Moreover, the optical measurement system of the present invention uses static polarization, i.e. the polarization of the light incident on the substrate is not varied during measurement, thus, the speed of the system is not limited by the rotation or modulation frequency of the optical elements of the system.

The static polarizing element can be a retarder for staticly elliptically, circularly, or linearly polarizing the light beam from the light source. The retarder can be, for example, a quarter-wave plate or a half-wave plate. In the alternative, the retarder can be a liquid crystal variable retarder (LCVR).

In a preferred embodiment of the invention, the optical measurement system can include a system for collecting and measuring scattered light reflected from the substrate surface to obtain information concerning the roughness of the substrate surface. The system for collecting and measuring scattered light can include an integrating sphere for collecting the scattered light and a photo-diode for measuring the intensity of the scattered light.

In one embodiment, the system includes a light source feedback system for controlling and stabilizing the light beam from the light source. The light source feedback system can include a photo-diode for measuring the intensity of the light beam and a light source controller for controlling and stabilizing the light beam based on the measured intensity. A non-polarizing beam splitter can be used to direct a portion of the light beam from the light source to the photo-iode for measurement. The light source feedback system can be integrated into the light source or, in the alternative, can be a separate, stand-alone sub-system of the illumination system of the optical measurement system of the present invention. Alternatively, the light source feedback system can be used solely to monitor the light beam from the light source, without control or stabilization of the light beam.

The optical system of the present invention preferably includes a controllable translatable assembly for moving the polarized light beam across a portion of the substrate. A position indicator can be employed to determine the particular locations on the substrate upon which the polarized light beam impinges. Preferably, the control systems compiles a data set, an image intensity map, correlating the measured amplitude of the s-polar and p-polar light with the particular location on the substrate upon which the light source impinges. The image intensity map can be stored in a memory storage device provided with the control system.

In one embodiment, the optical measurement system of the present invention, performs initial measurements on the substrate to generate an initial map of at least a portion of the substrate. A polarized light beam is directed to a plurality of measurement points on the substrate. The light from each measurement point on the substrate is separated into two orthogonally polarized light beams and the amplitude of each set of orthogonally polarized light beams is measured at a frequency of greater than 1 kHz. The control system compiles a data set, i.e. the initial map, by synchronizing the measured amplitude of each set of orthogonally polarized light beams with the location of each corresponding measurement point on the substrate. By comparison with a subsequent map, changes in the substrate, or a thin film layer overlying the substrate, can be resolved.

In accordance with another aspect of the present invention, the optical measurement system can provide for the measurement of at least three parameters simultaneously, thereby increasing the speed and time resolution of the system by requiring only a single scan of the substrate to analyze the substrate, while concomitantly increasing the sensitivity of the system to changes in the substrate surface or to changes in the thickness and optical characteristics of the thin film layer overlying the substrate. The measured parameters include the amplitude of the s-polarized and the p-polarized light components received from the substrate, as well as at least a third parameter, which can be, for example, the phase difference between the s-polarized and the p-polarized light components, the reflection angle of the light beam reflected from the substrate surface, or the amplitude of scattered light reflected from the substrate. Additionally, the present invention contemplates the simultaneous measurement of additional parameters, including all of the above-referenced parameters, as well as the simultaneous measurement of alternate combinations of these parameters.

According to further alternative embodiment of the present invention, the optical measurement system includes an intensity stabilized light source configured to generate a stabilized light beam, a polarizing element for polarizing the light beam emanating from the light source, and a detection system for measuring the light after interaction with the substrate. The detection system includes a polarization analyzing element for splitting the light after interaction with the substrate into s-polarized light and p-polarized light. The polarization analyzing element can be, for example, a polarizing beam splitter. The measurement system further includes two optical sensors for separately measuring the amplitude of the s-polarized light and the amplitude of the p-polarized light and a third optical sensor for measuring the phase difference between the s-polarized light and the p-polarized light. A control system is configured to analyze the measured amplitude of the s- and the p-polarized light and the phase difference to determine changes in the topography of substrate or changes in the thickness or optical characteristics of the thin film layer.

According to a further alternative embodiment of the present invention, the optical measurement system includes an intensity stabilized light source configured to generate a stabilized light beam, a polarizing element for polarizing the light beam emanating from the light source, and a detection system for measuring the light reflected from the substrate. The detection system includes a polarization analyzing elements for splitting the light after interaction with the substrate into s-polarized light and p-polarized light. The polarization analyzing element can be, for example, a polarizing beam splitter. The measurement system further includes two optical sensors for separately measuring the amplitude of the s-polarized light and the amplitude of the p-polarized light and a third optical sensor for measuring the reflection angle of the light reflected from the substrate. A control system is configured to analyze the measured amplitude of the s-polarized light and the p-polarized and the reflect angle to determine changes in the topography of substrate or changes thickness or optical characteristics of the thin film layer.

BRIEF DESCRIPTION OF THE DRAWINGS

These and other features and advantages of the present invention will be more fully understood by reference to the following detailed description in conjunction with the attached drawings in which like reference numerals refer to like elements and in which.

DETAILED DESCRIPTION

Figure 1:
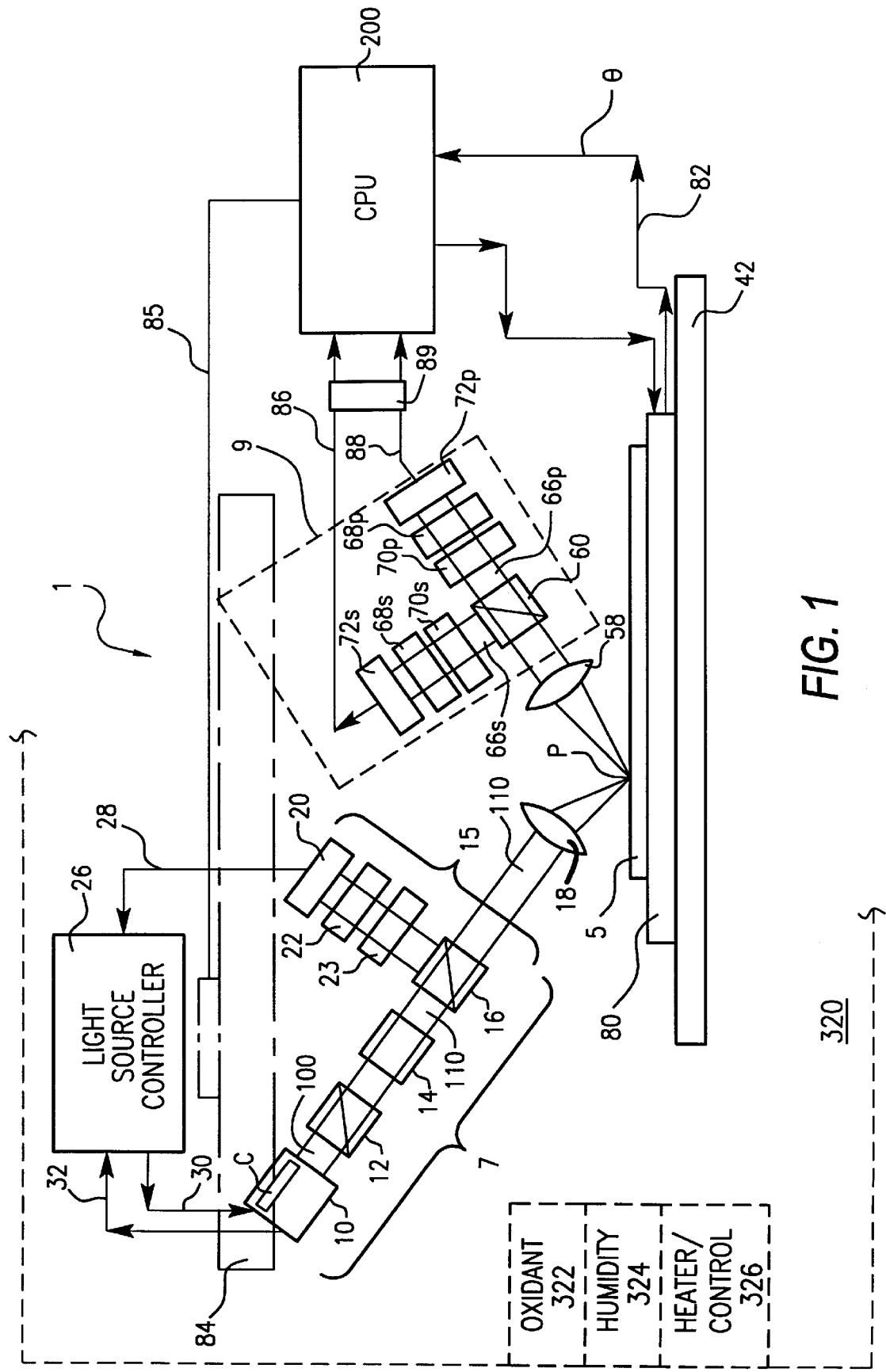
FIG. 1 is a schematic side view showing an optical measurement system in accordance with a first embodiment of the present invention.

An optical measurement system 1 for evaluating the topography of a substrate 5 and the thickness or optical characteristics of thin film layer overlying the substrate 5 in accordance with a first embodiment of the present invention is shown in FIG. 1. The components of the optical measurement system 1 include illumination system 7 for producing a polarized light beam and a detection system 9 for measuring the intensity of the polarized light reflected from the substrate.

The substrate 5 to be tested is supported by a test stand or base 42 and the illumination system 7 and the detection system 9 are movably suspended on a track Or stage 84 for one-dimensional translational movement along an axis perpendicular to the plane of the paper as shown in FIG. 1 over the base 42. Base 42 includes a motor driven turntable 80, e.g., a conventional so-called hard disk drive for rotating the substrate 5, for example a magnetic media storage disk, as well as a magnetic head and carrier of conventional type (not shown) for tribological testing of the disk as well as for reading information from and writing information onto the disk. Turntable 80 turns on a shaft (not shown) which has a 512 position shaft encoder, and corresponding angular position signals corresponding to a shaft rotation angle $s_{74}$ appear on line 82, which connects via appropriate circuitry to synchronize measurement acquisition in a processor, CPU 200. The position signals include a zero-position synchronization or framing signal, followed by the $2^{15}$ encoder signals, after suitable signal conditioning, in each rotation. The turntable may, for example, turn at 3,600 or 5,400 RPM, corresponding to thirty or forty-five thousand shaft encoder positions per second; if measurement speed is critical, a faster motor, for example, 7,200 RPM or 10,000 RPM, a more finely divided shaft encoder, and/or special control chips may be used to interpolate sample positions or otherwise increase the number of data points per second.

Above the turntable 80, the movable illumination system 7 and the detection system 9 are mounted so that they are positioned and aligned symmetrically about a probe a point P in the plane of disk 5. Movement of the assembly stage 84 scans the point P radially across the disk. Stage 84 is stepper controlled in one micrometer or less increments, and position indicating and control signals are continuously monitored or controlled by CPU 200 on line 85, to synchronize or coordinate the r, θ positions illuminated on the substrate 5 with optical results from the illumination system 7 and the detection system 9 which are provided to CPU 200, after suitable conditioning by A/D converter 89, along lines 86 and 88.

In the alternative, the turntable 80 or the base 42 can be mounted on a translatable table (not shown) to effect scanning of the point P across the surface of the substrate 5 as the turntable 80 rotates. In this arrangement, a separate stepper for stage 84 would be unnecessary.

The illumination system 7 can include a light source 10 which emits an intensity stabilized linearly polarized light beam 100. The light source 10 can be a laser source such as a four milliwatt laser diode producing a stable 670 nm output beam. The polarization quality of the light beam 100 can be improved by adding a polarizer 12 in the optical path after the light source 10. The light beam 100 is staticly elliptically, linearly, or circularly polarized by a retarder 14. If elliptically polarized, the light beam is preferably polarized to a polarization ratio of better than 100:1. The retarder 14 is preferably a zero-order quarter wave plate or, in the alternative, can be a liquid crystal variable retarder (LCVR) or a half wave plate (for linear polarized light). The LCVR permits increased control over the polarization of the light beam 100. For example, using the LCVR the light beam 100 can be linear polarized to one of the two orthogonal linear polarizations, s-polarization or p-polarization, in addition to being circularly or elliptically polarized.

Preferably, the polarization of the light beam 100 is stable, i.e. static, to optimize the speed of data acquisition of the system 1 during measurement. The polarization can be varied between measurements using the LCVR or by changing the retarder. For more sensitive measurements, modulation of the polarization of the beam 100 is possible using the LCVR, however, the speed of data acquisition may be reduced.

The polarized light 110 is focused to a small spot on the substrate 5 by objective 18. The objective 18 is can be a simple but high quality, e.g. diffraction limited, focusing assembly such as Melles Griot 06 GLC005, with a focal length of 48 mm. This produces approximately a 7 micron spot size from the laser diode output at the surface of the disk.

An external light source feedback system 15 can be provided in the optical path of the illumination system 7 to control and stabilize the intensity of the light source 10. The feedback system includes a non-polarizing beam splitter 16 and a photo-diode 20 for measuring the 90-degree light beam intensity. An optical diffuser 22 and a bandpass filter 23 can also be provided to reduce the possibility of stray light influencing the measurement of light source intensity at the photo-diode 20 and ensure the uniformity of the light reaching the photo-diode 20. A light source controller 26 receives the output signal from the photo-diode 20 along line 28 and generates a control signal along line 30 to control and stabilize light source 10. The light source controller 26 can be integrated into the light source 10, can be a part of separate external feedback control system or can be integrated into a central CPU 200 for controlling the optical measurement system 1. Internal feedback of the light source can occur through line 32.

In the alternative, the light source feedback system 15 can be used solely to monitor or measure the intensity of the light source 10. In this configuration, the intensity measurements from the light source feedback system can be monitored and later analyzed by CPU 200.

Within the light source 10 a temperature sensor which is integral with or contiguous to the laser diode is used to develop control signals for a solid state Peltier effect cooler C that is energized to maintain the laser cavity of the laser diode at a fixed temperature. This prevents the laser output from jumping between cavity modes as the laser operates. The laser is also operated at a constant output level. Such output control may be achieved in several ways. For example, beam splitter 16, which also may be formed integrally with the laser diode (such as by providing a partially transmissive, e.g., 0.01% transmissive, back face of the diode cavity) may provide a fixed portion of the output beam energy to photo-detector 20 to develop a laser amplitude signal, which is fed in a negative feedback loop to the laser current drive (light source controller 26), thus producing a constant amplitude laser output. Alternatively, rather than sensing and controlling laser output, a simple constant-current driver may be used. In this case a simple current feedback circuit stabilizes the drive signal level. With these two temperature and output stabilizing controls, the light source 10 produces a fixed wavelength output beam, with an amplitude that is constant to within one part in $10^4$.

The detection system 9 is mounted on the same stage or carriage as the illumination system 7 and is positioned at an equal angle of incidence over the substrate to receive the light beam reflected from the point P on the substrate. The detection system 9 includes a collimator 58 and a static polarizing beam splitter 60 which splits light reflected from the substrate 5 into two linear polarized light beam components, an s-polarized light beam 66s and a p-polarized light beam 66p. The detection system 9 includes two photo-diodes 72s and 72p for separately measuring the intensity of the s-polarized light beam 66s and the p-polarized light beam 66p, respectively. Thus, the photo-diodes 72s and 72p at each point in time produce an output indicative of the intensity of both the s-polarized light and the p-polarized light reflected from point P. Optical diffusers 68s and 68p and bandpass filters 70s and 70p can also be provided to reduce the possibility of stray light influencing laser intensity and ensure light uniformity. The optical diffusers 68s and 68p can each be replaced with an integrating sphere to decrease sensitivity to beam angle variations.

The substrate to be evaluated can be, for example, a magnetic storage disk of a standard commercial size, e.g., about sixty-five or ninety-five millimeters in diameter, and by way of example, may be formed of glass or of an aluminum/magnesium material about 1.9 mm thick. On the surface of a representative disk substrate is deposited a 10–15 micrometer thick nickel-phosphorous layer, followed by a layer of chromium about one thousand Angstroms thick. The actual magnetic storage layer is then laid down as a 500 Angstrom thick layer of a cobalt/platinum/chrome magnetic alloy medium. These layers form a totally reflective top of the disk. A planarizing layer of carbon about 150 Angstroms thick is then deposited over the magnetic storage layer, and a layer of lubricant, such as a perfluoropolyether with a thickness of about twenty Angstroms, is applied over the carbon layer.

A representative cycle of operation of the optical measurement system 1 proceeds as follows. The illumination system 7 provides a static elliptically (or linearly or circularly) polarized light beam 110, having both s-polarization components and p-polarization components, at a constant wavelength and intensity level monitored by the light source feedback system 15. As the turntable 80 rotates, the elliptically polarized light beam 110 is moved radially to step through the radial extent of the disk, and the CPU 200 stores digitized representations of the collected beam power for each point specified by coordinates (r, θ) on the disk, as measured by the detection system 9. This data collection provides a quantitative record or map of reflectance of all points on the substrate for the both s- and p-polarization states.

The optical measurement system 1 can be operated within a closed environmental test chamber 320, provided with heaters and temperature control system 326, together with suitable means for forming or connecting to sources 322, 324 of humidity, oxidant or other environmental agents which may be selectively actuated to expose the substrate surface to a variety of environmental test conditions. During such exposure, normal processing operations are carried out on the substrate to measure changes in the substrate surface. For example, in the case of a magnetic storage disk, a magnetic head is carried across the face of the disk over the lubricant layer, so various effects such as frictional wear, lubricant erosion or redistribution, and the like occur.

In a further representative protocol, following operation under the test conditions, a second set of reflectance measurements are made to compile a second map, or a comparative reflectance map, of the same substrate. During all this time, the substrate preferably remains on the turntable so that there is an exact correspondence between the points with fixed (r,θ) coordinate in each data set stored by the CPU 200.

Thus, if surface reflectance maps are made with s- and p-polarizations both before and after testing, one has available information on both the changes in s- and p-polarization reflectance, and the relative amounts of s- and p-polarization reflection at each time.

The optical system 1 of the present invention provides significant advantages over conventional optical measurement systems which use linear polarized light by permitting simultaneous measurement of s-polarized light and p-polarized light reflected from the substrate surface. In this manner, two separate scans, one for s-polarized light and one for p-polarized light, across the surface of the substrate are not necessary. This effectively doubles the data acquisition rate of the present system when compared with conventional linear polarizing systems, such as the apparatus disclosed in the copending U.S. application by the same inventor, Ser. No. 08/640,567, incorporated herein by reference.

In addition, the optical measurement system of the present invention offers many advantages over conventional reflection ellipsometers because a static analyzer, e.g., the polarizing beam splitter 60 is used in place of a conventional rotating analyzer. This permits data acquisition at increased speeds when compared to ellipsometers using a rotating or modulating optical element.

A significant advantage of the optical measurement system of the present invention is that the speed of data acquisition is limited primarily by the speed of the as system's electronics, in particular by the speed of the A/D converter 89. Thus, as higher speed electronics are made available, the instrument of the present invention can be used for real time and in Situ measurements of faster and faster disk drives. Presently, industry research is focused on obtaining disk drive speeds of approximately 10,000 RPM, however, disk drive speeds of 20,000 RPM may be possible. The optical instrument of the present invention affords the flexibility and adaptability to be configured to perform real time, in situ measurements of disks operating on such disk drives.

In the case of a magnetic storage disk operating on a hard disk drive, the magnetic head is designed to travel over the surface of the disk at a specific speed. Operating of the disk drive at a lower speed for extended periods of time can result in the head damaging the disk. Thus, it is important that any in situ measurements of the magnetic storage disk be performed at or near the operating speed of the hard disk drive to prevent the head from damaging the disk.

For example, a 95 mm magnetic storage disk rotating at a speed of 10,000 rpm can be measured in situ, i.e. within the disk drive, by the measurement system of the present invention. Using a laser spot size of 7 microns, 42636 data points can be measured per revolution without laser spot overlap. This corresponds to a data acquisition rate of approximately 7.1 MHz for full speed (10,000 RPM) data acquisition. For increased resolution, laser spot overlap between data points is preferred, thus the data acquisition rate of the present invention is preferably 10 MHz.

By using a 12 bit A/D converter, 0.1% variations in reflectivity , corresponding to changes in film thickness of approximately 10 angstrom, can be measured at the data acquisition rate of 10 MHz. Higher accuracy can be achieved at the 10 MHz data acquisition rate by applying variable offsets and gains. More precise measurements can be made without variable offsets and gains by using a 16 bit AID converter, however the data acquisition rate correspondingly decreases to the 200 kHz range. Conversely, the data acquisition rate can be increased into the 1 GHz range by using an 8 bit A/D converter, however, the corresponding loss of accuracy limits the application of such systems.

In general applications, the light beam 110 is preferably directed at an angle approximately equal to Brewster's angle of the material present on the substrate surface. In situations in which multiple thin film layers overlay the substrate surface, for example in the case of a magnetic storage disk, the light beam 110 is preferably directed at an angle φ of about 60°, and generally between about 53° and roughly 70°, so that tan (φ) lies between the index of refraction of the top thin film layer (e.g., the lubricant) and that of the bottom thin film layer (e.g., the carbon layer). By operating in a region where the light strikes above the Brewster's angle of one material (e.g., the lubricant) while being below the Brewster's angle for the other (the carbon layer) light of both polarizations will be represented in the collected light. Moreover, the relative amounts of detected s- and p-illumination, and the direction of change in intensity between two measurements can reveal the nature of changes in a simple logical array.

In general, the particular wavelength of the laser is not very important, since the lubricant film absorbs very little of the light at many available wavelengths, while the carbon film does absorb, but with a typical sensitivity which may be about 0.04% intensity change per Angstrom of film thickness. By stabilizing the laser source as described above, applicant is able to repeatably detect such small changes in amplitude. The temperature stabilization not only enhances the intensity stability, but further assures that beam 110 remains relatively free of mode hopping, so that diffractive jumps do not affect the intensity and wavelength; thus the (r,θ) coordinates taken at two different times will represent the same point P on the disk. The resolution of the reflectance map will in general depend on the spot size of the lens and the accuracy of the position monitoring means used to determine the location on the substrate.

The above apparatus has the great advantage of being quantitatively accurate, and of having a "perfect memory" of substrate coordinates when the substrate remains on the turntable. In the example of the magnetic storage disk, typically about seventy per cent of the s- polarized light is reflected, while less than half of the p-polarized light is reflected. Operating against a substantially perfectly reflective background, the total variation of intensity of the reflected light beam due to effects such as scattering, carbon thickness, and texture variation and absorbance is only about two percent. However, with the aforesaid apparatus, variations of 0.1% are readily detected, and the reflectance range is readily expanded to enhance image contrast. The coordinate/intensity map has therefore been found to be quite useful. For example, a very high resolution map of lubricant thickness is obtained by mapping the surface, rinsing the lubricant off, and then compiling a second reflectance map and comparing the two maps pointwise. The CPU 200 may include software modules to determine a pointwise difference map, to expand the range of detected intensity changes and to print out a graphic image of the substrate. It may also include pattern detection software to detect and to annotate specific features.

Moreover, in certain applications a single measurement scan or cycle of the substrate will be a sufficient evaluation of the substrate surface. In such applications, determination of the location of each measurement point on the substrate surface is unnecessary and, thus, the position encoder or the like can be removed from the system. Such applications include, for example, measuring the flatness of the substrate surface or evaluating the uniformity of a thin film applied to the substrate surface.

In addition, various enhanced measurement protocols may be implemented with the basic first embodiment discussed above.

The present system is useful in processes in which the film layer is deposited, etched, patterned, doped, oxidized, and annealed to evaluate changes in the thin film layer. For example, in sputtering processes in which a thin film layer is deposited onto a substrate, the optical measurement system of the present invention can be used to evaluate the optical characteristics as well as the thickness of the deposition layer to ensure uniform deposition thickness. The intensity of light measured by the detectors 72s and 72p of the optical measurement system is sensitive to changes in the refractive index and absorption coefficient of the deposited film and the substrate, as well as changes in the thickness of the film. Other specific examples include evaluating insulation layer thickness (i.e., silicon dioxide thickness) on a silicon wafer during semiconductor device manufacturing processes and analyzing thin film coatings used in thin film display panels.

Alternatively, the three-dimensional topography of a substrate can be evaluated during processing. For example, the optical measurement system of the present invention can be used to evaluate changes in the optical characteristics of silicon and gallium arsenide wafers in semiconductor and microelectronic manufacturing processes to measure film thickness and uniformity of, for example, oxide, nitride, and photoresist films.

Figure 2:
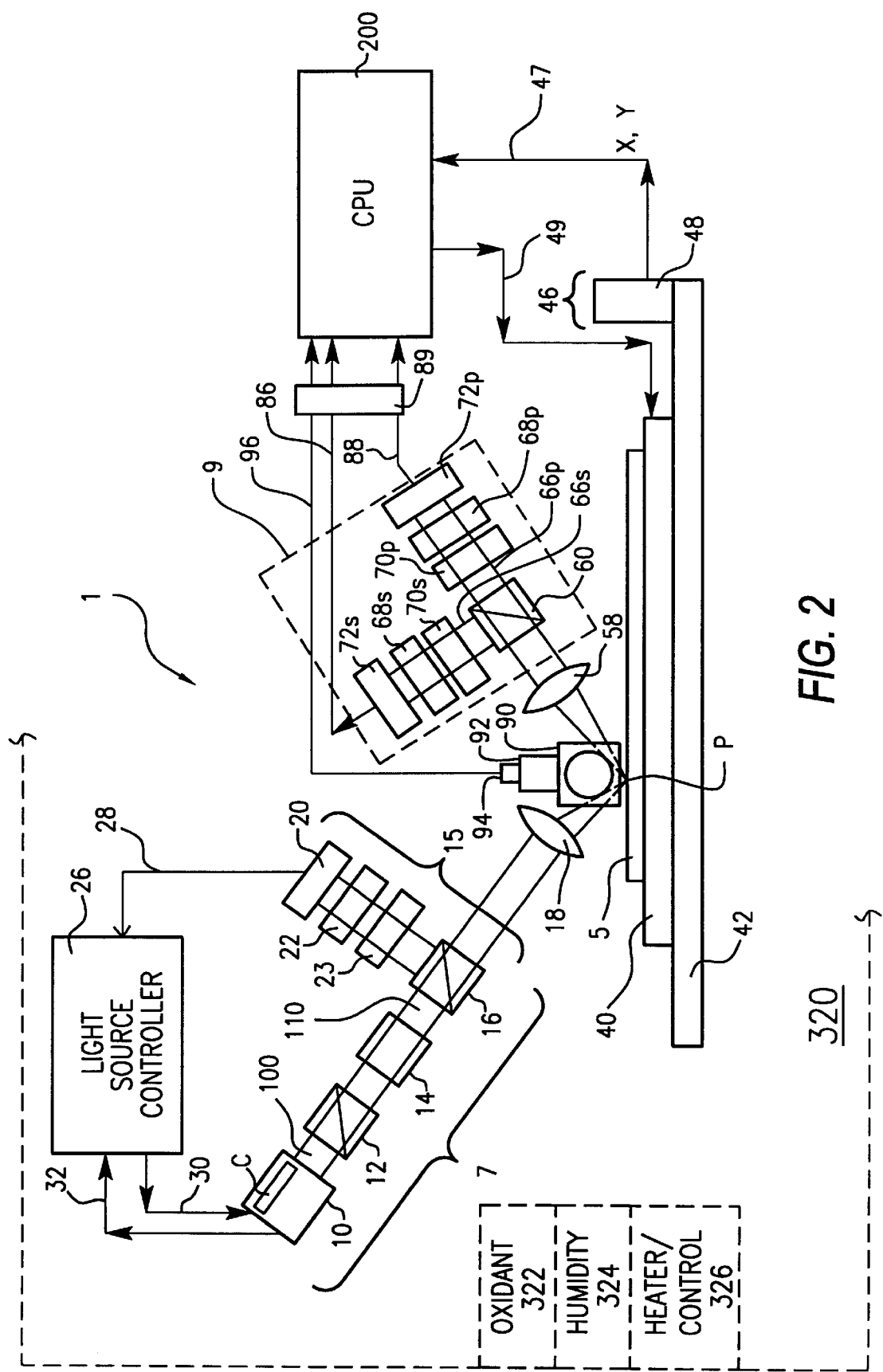
FIG. 2 is a schematic side view showing an optical measurement system in accordance with a second embodiment of the present invention.

A second embodiment of the optical measurement system of the present invention is shown in FIG. 2. In the second preferred embodiment, an integrating sphere 90 and filter 92 are provided above the substrate 5 to collect scattered light reflected from the substrate surface. The intensity of the scattered light is measured by photo-diode 94 and communicated to CPU 200 by line 96. The intensity of the scattered light measured by the integrating sphere 90 is sensitive to changes in substrate surface roughness and topography. Preferably, the integrating sphere 90 is positioned adjacent the substrate surface to maximize the amount of scattered light incident on the integrating sphere 90. In this position, light enters the integrating sphere 90 through the sides of the sphere. The integrating sphere 90 can alternatively be replaced with a diffuser.

Moreover, the turntable 80 and the stage 84 described in connection with the first embodiment (FIG. 1) can be replaced with alternative means for moving the substrate relative to the illumination system 7 and the detection system 9. For example, the substrate 5 can be supported by a conventional motor driven X-Y table 40, which is operable to move the substrate 5 in the X-Y plane and is in turn supported by a base 42, as shown in FIG. 2. A position monitoring system 46 is provided to precisely monitor the position of the substrate 5 relative to the illumination system. The position monitoring system 46 includes an encoder 48 mounted on the base 42 for determining the X position of the X-Y table and the substrate 5. A analogous encoder (not shown) is provided to determine the Y-position of the X-Y table and substrate 5. Positioning information from the encoders is provided to CPU 200 along line 47. The CPU 200 generates control signals, transmitted along line 49, for controlling X-Y position of the X-Y table and substrate 5 during testing.

Above the X-Y stage, the illumination system 7 and the detection system 9 are positioned and aligned symmetrically about a probe point P in the plane of the substrate 5. Movement of the X-Y table scans the point P across the substrate 5. The X-Y table is stepper controlled in one micrometer increments, and position indicating and control signals are continuously monitored and controlled by CPU 200 to synchronize the X-Y position on the substrate with results from the detection system 9.

Figure 3:
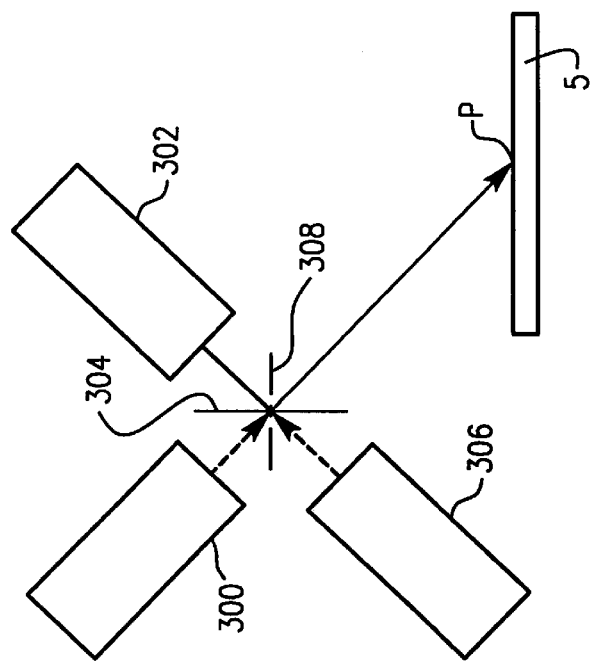
FIG. 3 is a schematic view showing the illumination system of an optical measurement system in accordance with a third embodiment of the present invention.

A third embodiment of the present invention is illustrated in FIG. 3, in which the illumination system is provided with two or more light sources for performing measurements at multiple wavelengths. For example, a first light source 300 operating at a first wavelength, a second light source 302 operating at a second wavelength, and a third light source 306 operating at a third wavelength can be provided within illumination system 7. Preferably each light source is individually stabilized. Suitable beam directing optics, for example mirrors 304 and 308, can be used to select a particular light source to illuminate the point P on the substrate 5. When multiple wavelengths of light are used, the retarder for polarizing the light beam is preferably an achromatic waveplate or an achromatic Fresnel rhomb.

During operation, the wavelength of light is preferably changed between scans of the substrate by alternating between the light sources. An exemplary measurement on the substrate can begin with a first scan of the substrate using the first light source 300 operating at the first wavelength. After completion of the first scan, the wavelength of light is changed by selecting the second light source 302 and a second scan is commenced at the second wavelength. A third scan is effected after completion of the second scan by selecting the third light source 306 to operate at the third wavelength. The information acquired from the three scans are then combined to obtain information about the optical properties and thickness of the substrate or the thin film overlying the substrate.

The advantage of performing measurements at different wavelengths is that additional information can be obtained concerning the optical properties or thickness of the substrate or thin films overlying the substrate than can be obtained in measurements performed at a single wavelength. Such additional information can be obtained by performing measurements at as few as two independent wavelengths. For more sensitive measurements, a greater number of wavelengths can be used, however, the time necessary for a complete evaluation of the substrate at all selected wavelengths is increased.

Figure 4:
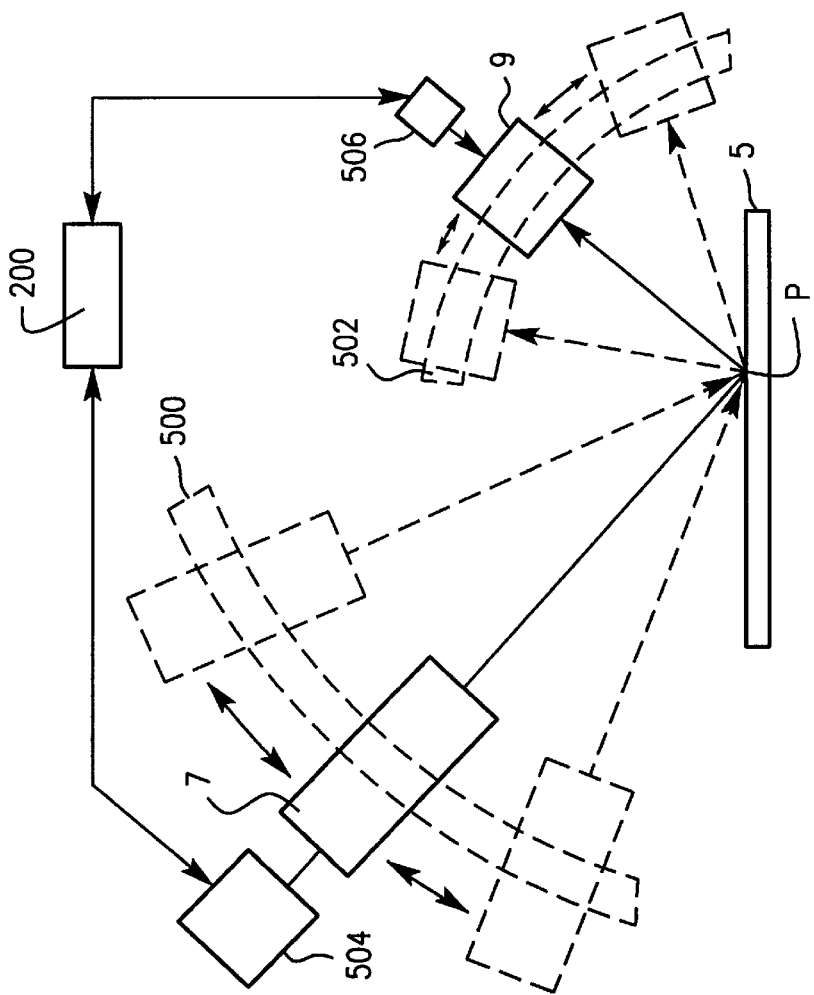
FIG. 4 is a schematic view showing the illumination system of an optical measurement system in accordance with a fourth embodiment of the present invention.

A fourth embodiment of the present invention is illustrated in FIG. 4, in which the illumination system 7 is movable to permit measurements at multiple angles of incidence. The illumination system 7 can be mounted on a rail 500 suspended above the substrate 5. Likewise, the detection system 9 can be mounted on a rail 502 to permit the detection system 9 to be moved in conjunction with the illumination system and thus maintain the same angle of incidence.

Movement of the illumination system 7 and the detection system 9 can be effected manually through a micrometer (not shown) or through a motor such as stepper motors 504 and 506. The stepper motors 504 and 506 are preferably controlled by CPU 200 to maintain a substantially identical angle of incidence for each of the systems. In the alternative, both the illumination system 7 and the detection system 9 can be mounted to a single rail to enable simultaneous change of the angle of incidence.

The operation of the fourth embodiment proceeds in a manner analogous to that of the third embodiment described above. Between scans of the substrate, the angle of incidence can be altered by adjusting the position of the illumination system 7 and the detection system 9 on the racks 500 and 502, respectively. Additional information about the optical properties and thickness of the substrate or a thin film overlying the substrate can be obtained by performing measurements at as few as two angles of incidence. For more sensitive measurements, additional angles of incidence can be used, however, the time required for a complete evaluation of the substrate at all the selected angles is increased.

Figure 5:
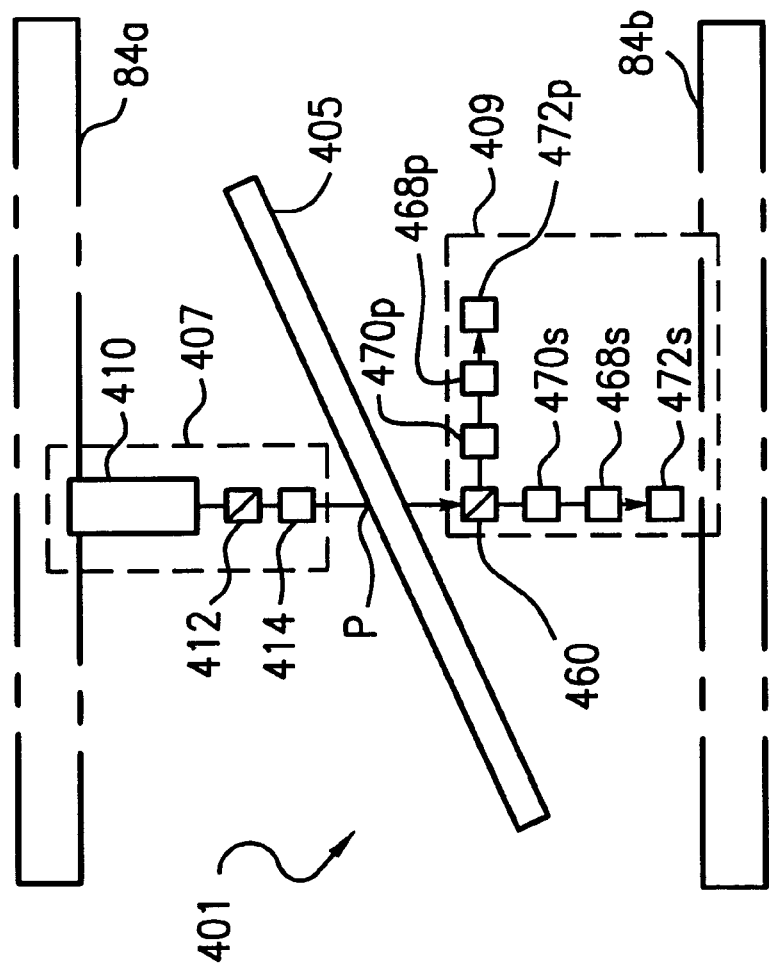
FIG. 5 is a schematic view showing an optical measurement system in accordance with a fifth embodiment of the present invention.

A fifth embodiment of the invention is illustrated in FIG. 5, in which the optical measurement system of the present invention is configured for transmissive measurement of an optically transparent substrate 405 such as, for example, glass substrates used in the fabrication of flat panel displays. The transmissive optical measurement system 401 includes an illumination system 407 configured in an analogous manner to the illumination system of the first embodiment. The illumination system 7 includes a light source 410 which emits a light beam, a polarizer 412, and a retarder 414 for staticly elliptically, linearly or circularly polarizing the light beam. An objective (not shown) can be used to focus the polarized light beam to the spot P on the transparent substrate 405.

The detection system 409 is positioned on the opposite side of the transparent substrate 405 relative to the illumination system 407. The detection system 409 is arranged in a manner analogous to the detection system of the first embodiment. The detection system 409 includes a static polarizing beam splitter 460 for splitting the transmitted polarized light into two linear polarized light beam components. Two photodiodes 472S and 472P measure the intensity of the s-polarized light and p-polarized light, respectively. Optical diffusers 468s and 468p and bandpass filters 470s and 470p are also provided to inhibit stray light from influencing laser intensity and ensure light uniformity.

The illumination system 407 and the detection system 409 can be movably suspended on separate tracks or stages 84a and 84b, respectively, for movement relative to the transparent substrate 405. In the alternative, the transparent substrate can be positioned on an X-Y stage (not shown) for movement relative to the illumination system 7 and the detection system 9.

A representative cycle of operation of the optical measurement system 401 proceeds as follows. The illumination system 407 provides a static elliptically (or linearly or circularly) polarized light beam having both s-polarization components and p-polarization components. The polarized light beam is moved across the surface of the optically transparent substrate 405 and received by detection system 409 after transmission through the substrate. The CPU 200 stores digitized representations of the transmitted beam power for each measurement point on the substrate as measured by the detection system 409. This data collection provides a quantitative map of all measurement points on the substrate for both s- and p-polarization states.

Figure 6:
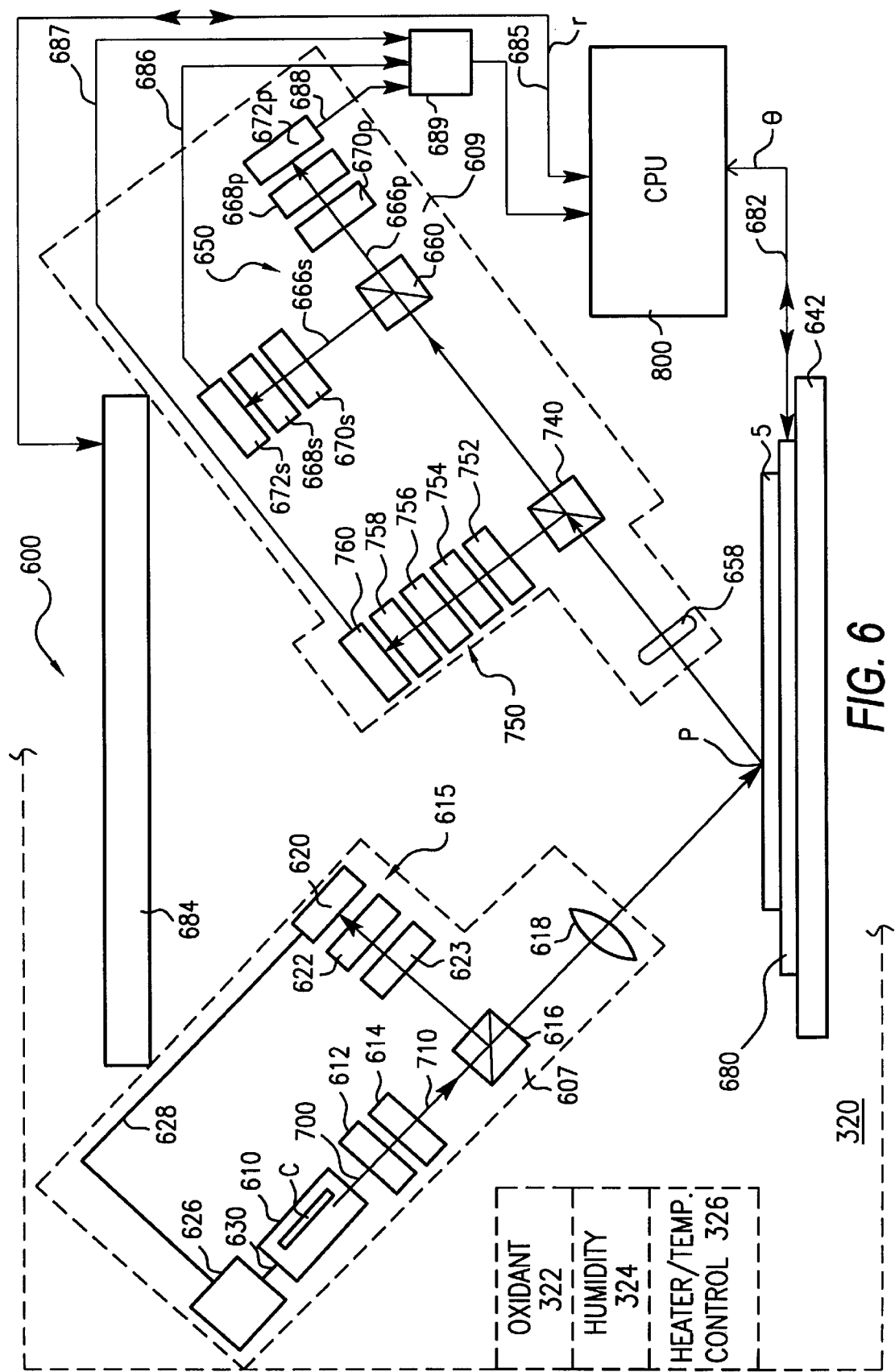
FIG. 6 is a schematic side view showing an optical measurement system in accordance with a sixth embodiment of the present invention.

An optical measurement system 600 for evaluating the topography of a substrate 5 and the thickness or optical characteristics of thin film layer overlying the substrate 5 in accordance with a sixth embodiment of the present invention is shown in FIG. 6. The components of the optical measurement system 600 include illumination system 607 for producing a polarized light beam and a detection system 609 for measuring the intensity and the phase difference of the components of the polarized light reflected from the substrate.

The substrate 5 to be tested is supported by a test stand or base 682 and the illumination system 607 and the detection system 609 are movably suspended on a track or stage 684 for one-dimensional translational movement along an axis perpendicular to the plane of the paper as shown in FIG. 6 over the base 642. Base 642 includes a motor driven turntable 680, e.g., a conventional so-called hard disk drive for rotating the substrate 5, for example a magnetic media storage disk, as well as a magnetic head and carrier of conventional type (not shown) for tribological testing of the disk as well as for reading information from and writing information onto the disk. Turntable 680 trans on a shaft (not shown) which has a 512 position shaft encoder, and corresponding angular position signals corresponding to a shaft rotation angle $s_\theta$ appear on line 682, which connects via appropriate circuitry to synchronize measurement acquisition in a processor, CPU 800. The position signals include a zero-position synchronization or framing signal, followed by the $2^{15}$ encoder signals, after suitable signal conditioning, in each rotation. The turntable may, for example, turn at 3,600 or 5,400 RPM, corresponding to thirty or forty-five thousand shaft encoder positions per second; if measurement speed is critical, a faster motor, for example, 7,200 RPM or 10,000 RPM, a more finely divided shaft encoder, and/or special control chips may be used to interpolate sample positions or otherwise increase the number of data points per second.

Above the turntable 680, the movable illumination system 607 and the detection system 609 are mounted so that they are positioned and aligned symmetrically about a probe a point P in the plane of disk 5. Movement of the assembly stage 684 scans the point P radially across the disk. Stage 684 is stepper controlled in one micrometer or less increments, and position indicating and control signals are continuously monitored or controlled by CPU 800 on line 685, to synchronize or coordinate the r, θ positions illuminated on the substrate 5 with optical results from the illumination system 607 and the detection system 609 which are provided to CPU 700, after suitable conditioning by A/D converter 689, along lines 686, 687, and 688.

In the alternative, the turntable 680 or the base 642 can be mounted on a translatable table (not shown) to effect scanning of the point P across the surface of the substrate 5 as the turntable 680 rotates. In this arrangement, a separate stepper for stage 684 would be unnecessary.

The illumination system 607 can include a light source 610 which emits an intensity stabilized linearly polarized light beam 700. The light source 610 can be a laser source such as a four milliwatt laser diode producing a stable 670 nm output beam. The polarization quality of the light beam 700 can be improved by adding a linear polarizer 612 in the optical path after the light source 610. The light beam 700 is preferably circularly polarized by a zero-order quarter wave plate 614 having an optic axis offset 45° from the optic axis of the polarizer 612. In the alternative, light beam 700 can be linearly polarized at 45° by rotating the light source 610 and the polarizer 612 by 45° about the optic axis and by eliminating the quarter wave plate 614. Additionally, the light beam 700 can be elliptically polarized, however, circular polarized light and 45° linear polarized light are preferred.

The polarized light 710 is focused to a small spot on the substrate 5 by objective 18. The objective 618 is can be a simple but high quality, e.g. diffraction limited, focusing assembly such as Melles Griot 06 GLC005, with a focal length of 48 mm. This produces approximately a 7 micron spot size from the laser diode output at the surface of the disk.

Within the light source 610 a temperature sensor, which is integral with or contiguous to the laser diode, is used to develop control signals for a solid state Peltier effect cooler C that is energized to maintain the laser cavity of the laser diode at a fixed temperature. This prevents the laser output from jumping between cavity modes as the laser operates.

The laser is preferably also operated at a constant output or intensity stabilized level. Such output control may be achieved in several ways. For example, an external light source feedback system 615 can provide a fixed portion of the output beam energy to photo-detector 620 to develop a laser amplitude signal, which is fed in a negative feedback loop to a laser current drive, light source controller 626, thus producing a constant amplitude laser output. An optical diffuser 622 and a bandpass filter 623 can also be provided to reduce the possibility of stray light influencing the measurement of light source intensity at the photo-diode 620 and ensure the uniformity of the light reaching the photo-diode 620. The light source controller 626 receives the output signal from the photo-diode 620 along line 628 and controls the output of the light source along line 630 to effect intensity stabilization of light source 610. The light source controller 626 can be integrated into the light source 610. The beam splitter 616 may be formed integrally with the laser diode (such as by providing a partially transmissive, e.g., 0.01% transmissive, back face of the diode cavity). In addition, the light source controller 626 can be part of a separate external feedback control system, as illustrated in FIG. 1, or can be integrated into central CPU 800.

Moreover, the light source feedback system 615 can be used solely to monitor or measure the intensity of the light source 610. In this configuration, the intensity measurements from the light source feedback system can be monitored and later analyzed by CPU 800. For example, light source intensity fluctuations occurring during a measurement procedure can be compensated for during analysis by the CPU 800 using the measured intensity provided by the feedback system 615.

The detection system 609 is mounted on the same stage or carriage as the illumination system 607 and is positioned at an equal angle of incidence over the substrate to receive the light beam reflected from the point P on the substrate. The detection system 609 includes a collimator 658 and a non-polarizing beam splitter 740 that splits the reflected light beam into two identical components for measurement by two detection sub-systems, a phase detection subsystem 750 and an intensity detection subsystem 650.

The phase detection subsystem includes a color filter 752 and a quarter wave plate 754 and a linear polarizer 756 which operate to analyze the degree to which the reflected light beam received from the beam splitter 740 is circularly polarized. The linear polarizer 756 is rotated 45° relative to the quarter wave plate 754. The circularly polarized reflected light beam is received by a photo detector 760 which measures the phase difference between the two orthogonally polarized components, i.e., the s-polarized component and the p-polarized component, of the reflected light beam. A diffuser 758 can be provided to inhibit the effect of substrate flatness on the measurement. It is also possible to omit the quarter wave plate 754 and use a 45° orientation for the polarizer 756.

The intensity detection subsystem 650 includes a polarizing beam splitter 660 which splits light reflected from the substrate 5 into two linear polarized light beam components, an s-polarized light beam 666s and a p-polarized light beam 666p. The detection system 609 includes two photo-diodes 672s and 672p for separately measuring the intensity of the s-polarized light beam 666s and the p-polarized light beam 666p, respectively. Thus, the photo-diodes 672s and 672p at each point in time produce an output indicative of the intensity of both the s-polarized light and the p-polarized light reflected from point P. Optical diffusers 668s and 668p and bandpass filters 670s and 670p can also be provided to reduce the possibility of stray light influencing laser intensity and ensure light uniformity. The optical diffusers 668s and 668p can each be replaced with an integrating sphere to decrease sensitivity to beam angle variations.

The substrate to be evaluated can be, for example, a magnetic storage disk of a standard commercial size, e.g., about sixty-five or ninety-five millimeters in diameter, and by way of example, may be formed of glass or of an aluminum/magnesium material about 0.8 mm thick. On the surface of a representative disk substrate is deposited a 10 . 15 micrometer thick nickel-phosphorous layer, followed by a layer of chromium about one thousand Angstroms thick. The actual magnetic storage layer is then laid down as a 500 Angstrom thick layer of a cobalt/platinum/chrome magnetic alloy medium. These layers form a totally reflective top of the disk. A planarizing layer of carbon about 150 Angstroms thick is then deposited over the magnetic storage layer, and a layer of lubricant, such as a perfluoropolyether with a thickness of about twenty Angstroms, is applied over the carbon layer.

A representative cycle of operation of the optical measurement system 600 proceeds as follows. The illumination system 607 provides a circularly or 45° linearly polarized light beam 710, having both s-polarization components and p-polarization components, at a constant wavelength and a constant intensity level monitored by the light source feedback system 615. As the turntable 680 rotates, the polarized light beam 710 is moved radially to step through the radial extent of the disk, and the CPU 800 stores digitized representations of the collected beam power and the phase difference for each point specified by coordinates (r,θ) on the disk, as measured by the detection system 609. This data collection provides a quantitative record or map of reflectance of all points on the substrate for the both s- and p-polarization states, as well as the phase difference between the s- and p-polarization states.

The optical measurement system 600 can be operated within a closed environmental test chamber 320, provided with heaters and temperature control system 326, together with suitable means for forming or connecting to sources 322, 324 of humidity, oxidant or other environmental agents which may be selectively actuated to expose the substrate surface to a variety of environmental test conditions. During such exposure, normal processing operations are carried out on the substrate to measure changes in the substrate surface. For example, in the case of a magnetic storage disk, a magnetic head is carried across the face of the disk over the lubricant layer, so various effects such as frictional wear, lubricant erosion or redistribution, and the like occur.

In a further representative protocol, following operation under the test conditions, a second set of reflectance measurements are made to compile a second map, or a comparative reflectance map, of the same substrate. During all this time, the substrate preferably remains on the turntable so that there is an exact correspondence between the points with fixed (r,θ) coordinate in each data set stored by the CPU 800.

Thus, if surface reflectance maps are made with s- and p-polarizations both before and after testing, one has available information on both the changes in s- and p-polarization reflectance and changes in the phase difference between the s- and p-polarizations, and the relative amounts of s- and p-polarization reflection at each time.

The optical system 600 of the present invention provides significant advantages over conventional optical measurement systems by permitting simultaneous measurement of at least three parameters: 1) the intensity of the s-polarized light component reflected from the substrate; 2) the intensity of the p-polarized light reflected from the substrate surface (collectively, the s- and p-polarization reflectance); and 3) the phase difference between the s- and p-polarization components reflected from the substrate. In this manner, separate scans for each parameter across the surface of the substrate are not necessary. This significantly increases the data acquisition rate of the present system when compared with prior art polarizing systems, such as the apparatus disclosed in the copending U.S. application by the same inventor, Ser. No. 08/640,567, incorporated herein by reference, while concomitantly increasing the sensitivity of the system to the changes in the substrate by providing additional information about the substrate in the form of an additional measurement parameter. The optical instrument of the present invention, thus, affords the flexibility and adaptability to be configured to perform accurate, real time, in situ measurements of the substrate under operation conditions or during production.

Measurement of the three parameters permits the calculation of three ellipsometric parameters: the amplitude ratio ψ, defined as the amplitude ratio of the p-polarization component to s-polarization component of the light reflected from the substrate surface, the phase difference Δ, defined as the difference in phase between the p-polarization component and the s-polarization component, and the total reflectivity r. The these ellipsometric parameters can be calculated from the following equations:

$$\psi = \tan^{-1}(R_p/R_s)^{1/2} \quad (1)$$

$$r = (R_p + R_s)/2 \quad (2)$$

$$\Delta = \cos^{-1}(+/-(2*R_{ph} - (R_p + R_s)/2)/(R_p*R_s)^{1/2} \quad (3)$$

where $R_p$ is the output from photo detector 672p, $R_s$ is the output from photo detector 672s, and $R_{ph}$ is the output from photo detector 760.

Measurement of the total reflectivity r is possible with the optical measurement system of the present invention because photo detectors 672s and 672p measure the absolute reflectivity or intensity of the s- and p-polarization components. Because the incident illumination provided by prior art ellipsometers is typically less stable, prior art ellipsometers measure the ratio of the polarization components instead of the absolute reflectivity or intensity of the s- and p-polarization components and, thus, can not calculate the total reflectivity r. In contrast, the highly stabilized light source of the optical measurement system of the present invention permits direct measurement of the absolute reflectivity of the individual polarization components, and, thus, the determination of total reflectivity r.

In general applications, the light beam 710 is preferably directed at an angle approximately equal to Brewster's angle of the material present on the substrate surface. In situations in which multiple thin film layers overlay the substrate surface, for example in the case of a magnetic storage disk, the light beam 710 is preferably directed at an angle φ of about 60°, and generally between about 53° and roughly 70°, so that tan (φ) lies between the index of refraction of the top thin film layer (e.g., the lubricant) and that of the bottom thin film layer (e.g., the carbon layer). By operating in a region where the light strikes above the Brewster's angle of one material (e.g., the lubricant) while being below the Brewster's angle for the other (the carbon layer) light of both polarizations will be represented in the collected light. Moreover, the relative amounts of detected s- and p-illumination, and the direction of change in intensity between two measurements can reveal the nature of changes in a simple logical array.

In general, the particular wavelength of the laser is not very important, since the lubricant film absorbs very little of the light at many available wavelengths, while the carbon film does absorb, but with a typical sensitivity which may be about 0.04% intensity change per Angstrom of film thickness. By stabilizing the output of the laser source as described above, applicant is able to repeatably detect such small changes in amplitude. The temperature stabilization not only enhances the intensity stability, but further assures that beam 710 remains relatively free of mode hopping, so that mode hops do not affect the intensity and wavelength; thus the (r,θ) coordinates taken at two different times will represent the same point P on the disk. The resolution of the reflectance map will in general depend on the spot size of the lens and the accuracy of the position monitoring means used to determine the location on the substrate.

The above apparatus has the advantage of being quantitatively accurate, and of having a "perfect memory" of substrate coordinates when the substrate remains on the turntable. In the example of the magnetic storage disk, typically about seventy per cent of the s- polarized light is reflected, while less than half of the p-polarized light is reflected. Operating against a substantially perfectly reflective background, the total variation of intensity of the reflected light beam due to effects such as scattering, carbon thickness, and texture variation and absorbance is only about two percent. However, with the aforesaid apparatus, variations of 0.1% are readily detected, and the reflectance range is readily expanded to enhance image contrast. The coordinate/intensity map has therefore been found to be quite useful. For example, a very high resolution map of lubricant thickness is obtained by mapping the surface, rinsing the lubricant off, and then compiling a second reflectance map and comparing the two maps pointwise. The CPU 800 may include software modules to determine a pointwise difference map, to expand the range of detected intensity changes and to print out a graphic image of the substrate. It may also include pattern detection software to detect and to annotate specific features.

Moreover, in certain applications a single measurement scan or cycle of the substrate will be a sufficient evaluation of the substrate surface. In such applications, determination of the location of each measurement point on the substrate surface is unnecessary and, thus, the position encoder or the like can be removed from the system. Such applications include, for example, measuring the flatness of the substrate surface or evaluating the uniformity of a thin film applied to the substrate surface.

The present system is useful in processes in which the film layer is deposited, etched, patterned, doped, oxidized, and annealed to evaluate changes in the thin film layer. For example, in sputtering processes in which a thin film layer is deposited onto a substrate, the optical measurement system of the present invention can be used to evaluate the optical characteristics as well as the thickness of the deposition layer to ensure uniform deposition thickness. The intensity of light measured by the detectors 672s, 672p, and 760 of the optical measurement system is sensitive to changes in the refractive index and absorption coefficient of the deposited film and the substrate, as well as changes in the thickness of the film. Other specific examples include evaluating insulation layer thickness (i.e., silicon dioxide thickness) on a silicon wafer during semiconductor device manufacturing processes and analyzing thin film coatings used in thin film display panels.

Alternatively, the three-dimensional topography of a substrate can be evaluated during processing. For example, the optical measurement system of the present invention can be used to evaluate changes in the optical characteristics of silicon and gallium arsenide wafers in semiconductor and microelectronic manufacturing processes to measure film thickness and uniformity of, for example, oxide, nitride, and photoresist films.

In addition, various enhanced measurement protocols may be implemented with the sixth embodiment discussed above.

Figure 7:
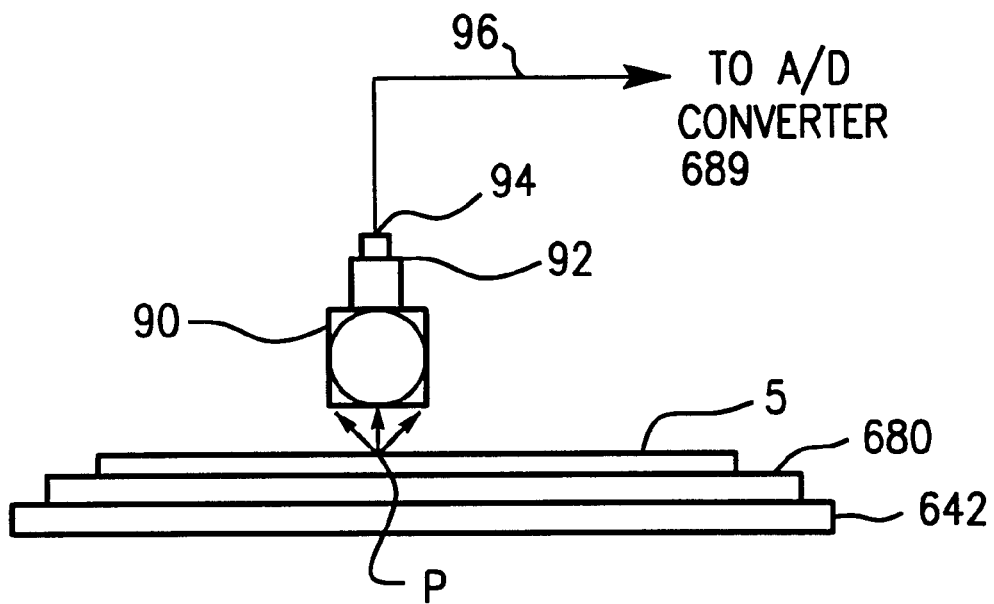
FIG. 7 is a schematic side view showing a system for measuring scattered light in accordance with the teachings of the present invention.

An alternative embodiment of the optical measurement system of the present invention is shown in FIG. 7. In this embodiment, an integrating sphere 90 and filter 92 are provided above the substrate 5 to collect scattered light reflected from the substrate surface. The intensity of the scattered light is measured by photo-diode 94 and communicated to A/D converter 689 by line 96. The intensity of the scattered light measured by the integrating sphere 90 is sensitive to changes in substrate surface roughness and topography. Preferably, the integrating sphere 90 is positioned adjacent the substrate surface to maximize the amount of scattered light incident on the integrating sphere 90. In this position, light enters the integrating sphere 90 through the sides of the sphere. The integrating sphere 90 can alternatively be replaced with a diffuser.

Inclusion of the integrating sphere 90 allows the optical measurement system of the present invention to measure four parameters of the reflected light beam simultaneously in a single scan of the substrate: 1) the intensity of the s-polarized light component; 2) the intensity of the p-polarized (collectively, the s- and p-polarization reflectance); 3) the phase difference between the s- and p-polarization components; and 4) the intensity of scattered light.

Figure 8:
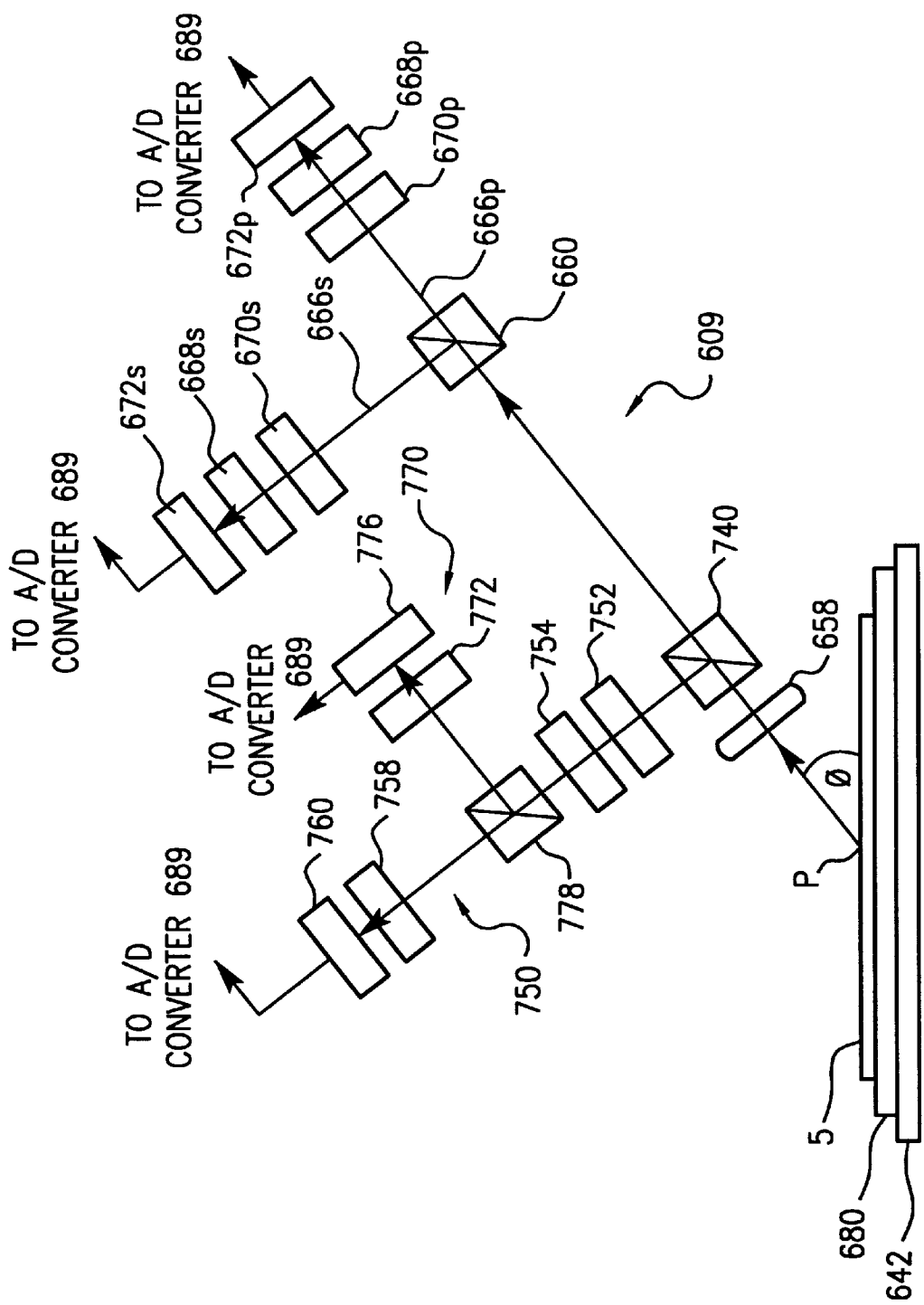
FIG. 8 is a schematic side view showing the detection system of an optical measurement system in accordance with a further alternative embodiment of the present invention.

A further alternative embodiment of the present invention is illustrated in FIG. 8, in which the detection system 609 of the present invention includes an additional detection subsystem 770 for determining the reflection angle of the reflected light beam during a measurement scan. The term "reflection angle" as used herein is inclusive of both the polar angle φ, illustrated in FIG. 8, and the azimuthal angle θ (not shown). Measurement of the reflection angle provides a direct measurement of the long spatial wavelength roughness, such as waviness or flatness, of the sample under evaluation, as the reflection angle for each measurement point P is dependent on the angle of the substrate surface at the point P. Inclusion of the reflection angle detection subsystem 770 allows the optical measurement system of the present invention to measure four parameters of the reflected light beam simultaneously in a single scan of the substrate: 1) the intensity of the s-polarized light component; 2) the intensity of the p-polarized (collectively, the s- and p-polarization reflectance); 3) the phase difference between the s- and p-polarization components; and 4) the reflection angle. Moreover, by adding integrating sphere 90, as discussed above in connection with the description of the second embodiment, an additional fifth component, the intensity of scattered light, can also be simultaneously measured.

The reflection angle detection subsystem 770 includes a quadrant photo detector 776, available from UDT Sensors, Inc. of Hawthorne, Calif., as well as, a band pass filter 772. The linear polarizing element 756 of the phase detection subsystem 750 can be replaced with a polarizing beam splitting cube 778 which produces two beams, one received by photo detector 760 and the other received by quadrant photo detector 776. In the alternative, a separate non-polarizing beam splitter (not shown) can be provided in the optic path between beam splitter 740 and the photo detector 760 to direct a portion of the reflected light to the quadrant photo detector 776.

It is to be understood that the present invention is not limited to the embodiments described above, but encompasses any and all embodiments within the scope of the following claims:

1. An optical measurement system for evaluating a substrate area, the system comprising:
    a laser source including a feedback system for generating an intensity-stabilized light beam,
    a polarizing element for polarizing the light beam emanating from the laser system to provide stabilized polarized light,
    an optical element for directing the stabilized polarized light to a particular location on the substrate,
    a translatable assembly to enable relative motion of the polarized light beam relative to at least a portion of the substrate so that the polarized light beam impinges on multiple locations in a two dimensional field on the substrate,
    a detection system for measuring the light beam after interaction with the particular location on the substrate, the detection system including
        a beam splitting element for splitting the light beam after interaction with the particular location on the substrate into s-polarized light and p-polarized light,
        a first sensor for measuring amplitude of the s-polarized light,
        a second sensor for measuring amplitude of the p-polarized light, and
    a control system for controlling said translatable assembly and measuring the location of the light beam in said field on the substrate.

2. The optical measurement system of claim 1, wherein the laser is a fiber-coupled laser diode.

3. The optical measurement system of claim 1, wherein the laser is a laser diode.

4. The optical measurement system of claim 1, wherein the polarizing element is a retarder.

5. The optical measurement system of claim 4, wherein the retarder is a quarter-wave plate.

6. The optical measurement system of claim 4, wherein the retarder is a liquid crystal variable retarder (LCVR).

7. The optical measurement system of claim 1, wherein the optical element is an objective lens.

8. The optical measurement system of claim 1, wherein the beam splitting element is a polarizing beam splitter.

9. The optical measurement system of claim 1, wherein the first sensor and the second sensor are photo-diodes.

10. The optical measurement system of claim 9, further comprising a light source feedback system for controlling and stabilizing the intensity of the light beam and wherein the light source feedback system includes a photo-diode for measuring the intensity of the light beam and generating an output signal based on the measured intensity, and
    a light source controller coupled to the light source and the photo-diode, the light source controller controlling and stabilizing the light beam based on the output signal received from the photo-diode.

11. The optical measurement system of claim 10, further comprising a non-polarizing beam splitter for directing a portion of the light beam to the photo-diode.

12. The optical measurement system of claim 1, further comprising a light source feedback system for monitoring the intensity of the light beam.

13. The optical measurement system of claim 18, wherein the light source feedback system includes a photodiode for measuring the intensity of the light beam.

14. The optical measurement system of claim 1, in which the measuring system for the location of the light beam comprises a position indicating means for determining the particular location on the substrate upon which the polarized light beam impinges.

15. The optical measurement system of claim 14, wherein the position indicating means is a 512 position shaft encoder.

16. The optical measurement system of claim 15, wherein the control system is coupled to the position indicating means, the first sensor for measuring amplitude of s-polarized light, and the second sensor for measuring amplitude of p-polarized light, the control system compiling a data set correlating the measured amplitude of the s-polarized light and the p-polarized light with the particular locations on the substrate upon which the light beam impinges.

17. The optical measurement system of claim 16, wherein the control system includes memory for storing the data set.

18. The optical measurement system of claim 1, wherein the polarizing element is an electrical elliptical polarizer for elliptically polarizing the light beam.

19. The optical measurement system of claim 1, wherein the polarizing element is a linear polarizer for linearly polarizing the light beam.

20. The optical measurement system of claim 1, wherein the polarizing element is a circular polarizer for circularly polarizing the light beam.

21. The optical measurement system of claim 1 further comprising a system for collecting and measuring scattered light reflected from the substrate.

22. The optical measurement system of claim 21, wherein the system for collecting and measuring scattered light includes an integrating sphere.

23. A method of evaluating a substrate comprising the steps of generating an initial map of at least a portion of the substrate by:
    generating an intensity-stabilized laser light beam by using a laser source and feedback,
    polarizing the light beam to form a stabilized polarized light beam,
    directing the polarized laser light beam to a measurement point on the substrate,
    relatively transporting the polarized light beam to at least one new measurement point on the substrate in a two dimensional field,
    separating the polarized light beam after interaction with a particular location on the substrate into a set of two orthogonally polarized light beams,
    measuring the amplitude of each of the orthogonally polarized light beams,
    compiling a data set by synchronizing the measured amplitude of each set of orthogonally polarized light beams with the location of each corresponding measurement point on the substrate;
    thereafter following the aforesaid steps and generating a second map of said portion of the substrate; and
    determining changes in the substrate by comparing the initial map with the second map.

24. The method of claim 23 wherein the step of polarizing the light beam includes the step of linearly polarizing the light beam.

25. The method of claim 23, wherein the step of polarizing the light beam includes the step of elliptically polarizing the light beam.

26. The method of claim 23, wherein the step of polarizing the light beam includes the step of circularly polarizing the light beam.

27. An optical measurement system for evaluating a substrate, the system comprising:

an intensity stabilized light source including a feedback system configured to generate an intensity stabilized light beam a polarizing element for polarizing the light beam emanating from the light generating source to provide stabilized polarized light, an optical element for focusing the stabilized polarized light at a particular location on the substrate, a controllable translatable assembly to create relative movement between the focused stabilized polarized light and the substrate to move the location of the focused stabilized light over a two dimensional field on the substrate, a detection system for measuring the light beam reflected from the particular location on the substrate, the detection system including a beam splitting element to split the light beam reflected from the particular location on the substrate into s-polarized light and p-polarized light, a first sensor for measuring amplitude of the s-polarized light, a second sensor for measuring amplitude of the p-polarized light, and a CPU for controlling said translatable assembly and for determining the location of the light beam and for analyzing the measured amplitude of the s-polarized light and the p-polarized light to determine characteristics of the substrate.

28. An optical measurement system for evaluating a substrate, the system comprising:

an intensity stabilized light source employing a feedback mechanism configured to generate an intensity stabilized light beam, a polarizing element for polarizing the light beam emanating from the light source to provide a polarized light beam, an optical system for directing the polarized light beam to a particular location on the substrate, a controllable translatable assembly for moving the polarized light beam across at least a portion of the substrate in a two dimensional field such that the polarized light beam impinges upon multiple locations on the substrate, a position indicator for determining the particular location on the substrate upon which the polarized light beam impinges, a detection system configured to evaluate the light beam after interaction with the particular locations on the substrate upon which the polarized light beam impinges, the detection system including a polarization analyzing element for separating the light from the particular locations on the substrate into s-polarized light and p-polarized light, a first optical sensor measuring amplitude of the s-polarized light, a second optical sensor measuring amplitude of the p-polarized light, and a control system for controlling said translatable assembly and said position indicator for determining the particular location of the light beam, configured to compile a data set correlating the measured amplitude of the s-polarized light and the p-polarized light with the particular location on the substrate upon which the polarized light beam impinges.

29. The optical measurement system of claim 28, wherein a light source feedback system controls and stabilizes the intensity of the light beam.

30. The optical measurement system of claim 29, wherein the light source feedback system includes a photo-diode for measuring the intensity of the light beam and generating an output signal based on the measured intensity, and a light source controller coupled to the light source and the photo-diode, the light source controller controlling and stabilizing the light beam based on the output signal received from the photo-diode.

31. The optical measurement system of claim 30, further comprising a non-polarizing beam splitter for directing a portion of the light beam to the photo-diode.

32. The optical measurement system of claim 28, further comprising a system for measuring scattered light after interaction of the light beam with the substrate.

33. The optical measurement system of claim 32, wherein the system for collecting and measuring scattered light includes an integrating sphere.

34. The optical measurement system of claim 28, wherein the detection system further includes a non-polarizing beam splitter directing a portion of the light beam after interaction with the substrate to the third optical sensor.

35. The optical measurement system of claim 28, wherein the polarization analyzing element is a polarizing beamsplitter.

36. The optical measurement system of claim 28, further comprising a light source monitoring system for monitoring the intensity of the light beam.

37. A method of evaluating a substrate comprising the steps of generating an intensity stabilized light beam;

polarizing the light beam to form a polarized light beam;

directing the polarized light beam to a particular location in a two dimensional field on the substrate;

separating the polarized light beam after interaction with the particular location on the substrate into two orthogonally polarized light beams;

controlling the directed light beam onto locations in said two dimensional field and determining the locations of the directed light beam; and analyzing the measured amplitude of each of the two orthogonally polarized light beams and the measured phase difference between the two orthogonally polarized light beams for various locations in said two dimensional field to determine changes in the substrate.

38. The method of claim 37, further comprising the steps of monitoring the intensity of the light beam, and controlling and stabilizing the intensity of the light beam based on the monitored light intensity.

39. The method of claim 37, further comprising the steps of measuring scattered light after the light beam interacts with the substrate and wherein the step of analyzing includes analyzing the measured scattered light to determine changes in the substrate.

40. A method of evaluating a substrate area comprising the steps of:

generating an intensity-stabilized light beam using a laser source with a feedback system;

polarizing the light beam from said laser source to form a stabilized polarized light beam;

directing the stabilized polarized light beam to a point for measurement on the substrate;

relatively transporting the polarized light beam to a plurality of additional measurement points on the substrate within a two dimensional field so that the polarized light beam impinges on multiple locations on said substrate within said field detecting the light beam after interaction with the substrate in said field including:

splitting the light beam after interaction with a location on said substrate into s-polarized light and p-polarized light and measuring the amplitude of the s-polarized light with a first sensor, and measuring the amplitude of the p-polarized light with a second sensor, and controlling the transport of said polarized light beam while determining the location of the light beam on the substrate for compiling a data set for each measurement of said first and second sensors to determine characteristics of the substrate.

41. A method of evaluating a substrate comprising the steps of generating an intensity stabilized light beam;

polarizing the light beam to form a polarized light beam;

directing the polarized light beam to particular locations in a two dimensional field on the substrate;

controlling the directed light beam onto locations in said two dimensional field and determining the impinging locations of the directed light beam; and analyzing the measured phase difference between the two orthogonally polarized light beams for various locations in said two dimensional field to determine surface characteristics of the substrate.

* * * * *

UNITED STATES PATENT AND TRADEMARK OFFICE
Certificate

Patent No. 6,307,627 B1                                  Patented: October 23, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Gerard H. Vurens, Palo Alto, CA; and David L. Klein, Santa Clara, CA.

Signed and Sealed this Thirty-first Day of August 2004.

*GREGORY J. TOATLEY, JR.*
*Supervisory Patent Examiner*
*Art Unit 2877*